United States Patent
Lantzsch et al.

(10) Patent No.: US 6,372,916 B2
(45) Date of Patent: Apr. 16, 2002

(54) METHOD FOR PRODUCING TRIAZOLINETHIONE DERIVATIVES

(75) Inventors: Reinhard Lantzsch, Wuppertal; Manfred Jautelat, Burscheid; Achim Hupperts, Düsseldorf, all of (DE); David Erdman, Liberty, MO (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/750,589

(22) Filed: Dec. 28, 2000

Related U.S. Application Data

(62) Division of application No. 09/509,889, filed as application No. PCT/EP98/06111 on Sep. 25, 1998, now Pat. No. 6,271,389.

(30) Foreign Application Priority Data

Oct. 8, 1997 (DE) .......................................... 197 44 401

(51) Int. Cl.⁷ .......................................... C07D 249/12
(52) U.S. Cl. .................................................. 548/263.2
(58) Field of Search ...................... 548/263.2

(56) References Cited

FOREIGN PATENT DOCUMENTS

| EP | 784053 | 7/1997 |
|----|--------|--------|
| WO | 96/16048 | 5/1996 |

OTHER PUBLICATIONS

*Isamu Arai, "Reactions of Phenylhydrazinium Thiocyanate With Ketones and Aldehydes", Bulletin of the Chemical Society of Japan, vol. 46, No. 7, (month unavailable) 1973, pp. 2215–2218, XP002090972.
*Chemical Abstracts, vol. 95, No. 23, Dec. 7, 1981, Columbus, Ohio, US; Abstract No. 203899, G. Gadzhiev et al, "Reaction of Ethanol Hydrazones With Isocyanates", XP00209073.
*Chemical Abstracts, vol. 88, No. 11, Mar. 13, 1978, Columbus, Ohio, US, Abstract No. 74395, O. Wakabayashi et al "1,2–Substituted–3–Alkoxycarboimino–4–substituted S–triazolidine–5–Thiones" XP002090974.

*Primary Examiner*—Patricia L. Morris
(74) *Attorney, Agent, or Firm*—Joseph C. Gil; Raymond J. Harmuth

(57) ABSTRACT

According to a novel process, it is possible to prepare triazolinethione derivatives of the formula

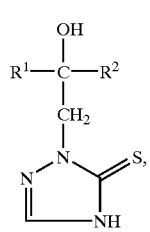

(I)

in which $R^1$ and $R^2$ are each as defined in the description by a) reacting hydrazine derivatives of the formula

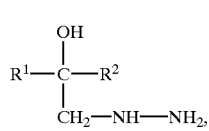

(II)

with carbonyl compounds of the formula

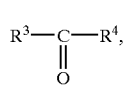

(III)

in which $R^3$ and $R^4$ are each as defined in the description with potassium thiocyanate, sodium thiocyanate or ammonium thiocyanate, if appropriate in the presence of a diluent and if appropriate in the presence of an acid, and b) reacting the resulting triazolidinethione derivatives of the formula

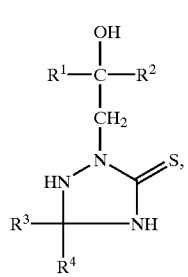

(V)

with formic acid, if appropriate in the presence of a catalyst and if appropriate in the presence of a diluent.

The triazolidinethione derivatives of the formula (V) are novel.

6 Claims, No Drawings

METHOD FOR PRODUCING TRIAZOLINETHIONE DERIVATIVES

This application is a divisional of Ser. No. 09/509,889 filed Apr. 3, 2000 now U.S. Pat. No. 6,271,389 B1.

The present invention relates to a novel process for preparing triazolinethione derivatives which are known as active compounds having microbicidal, in particular fungicidal, properties.

It is already known that triazolinethione derivatives can be prepared by either reacting the corresponding triazole derivatives successively with strong bases and sulphur and then hydrolysing them, or reacting them directly with sulphur at high temperatures, followed by treatment with water (cf. WO-A 96-16 048). However, this process has the disadvantage that the desired products are obtained in only relatively low yields, or that reaction conditions are required which are difficult in maintained on an industrial scale.

Furthermore, it has already been described that certain 1,2,4-triazoline-5-thiones substituted in the 3 position can be prepared by reacting N-chlorothioformyl-N-(1-chloroalk-1-ene)-amines with carbonylhydrazine derivatives (cf. DE-A-197-01-032, DE-A 196 01 189 and EP-A 0 784 053). However, the synthesis of corresponding substances which do not have a substituent in the 3 position is not mentioned.

Furthermore, Bull. Chem. Soc. Japan 46, 2215 (1973) discloses that triazolinethiones substituted in the 3 position can be synthesized by reacting phenylhydrazine with sodium thiocyanate and ketones or aldehydes in the presence of hydrochloric acid and treating the resulting triazolidinethiones substituted in the 3 position with oxidizing agents. This process has the disadvantages that very long reaction times are required and that no triazolinethiones which are unsubstituted in the 3 position can be obtained in this manner.

Finally, it is also known that 2-(1-chloro-cyclopropyl)-1-(2-chloro-phenyl)-3-(1,2,4-triazol-1-yl)-propan-2-ol is obtained when [1-(2-chloro-phenyl)-2-(1-chloro-cyclopropyl)- 2-hydroxy]-propyl-1-hydrazine is reacted with formamidine acetate (cf. DE-A-40 30 039). However, thiono derivatives of triazoles are not obtainable by this method.

It has new been found that triazolinethione derivatives of the formula

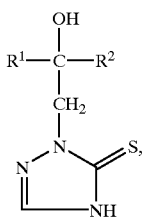

(I)

in which
R$^1$ and R$^2$ are identical or different and each represents optionally substituted alkyl, optionally substituted alkenyl, optionally substituted cycloalkyl, optionally substituted aralkyl, optionally substituted aralkenyl, optionally substituted aroxyalkyl, optionally substituted aryl or optionally substituted heteroaryl, can be prepared by
a) reacting, in a first step, hydrazine derivatives of the formula

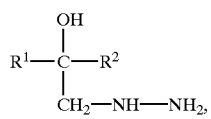

(II)

in which
R$^1$ and R$^2$ are each as defined above with carbonyl compounds of the formula

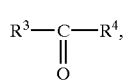

(III)

in which
R$^3$ represents alkyl having 1 to 4 carbon atoms or represents phenyl and
R$^4$ represents hydrogen or alkyl having 1 to 4 carbon atoms or
R$^3$ and R$^4$ together represents a —(CH$_2$)$_5$— than
and with thiocyanate of the formula

X—SCN (IV), in which
X represents sodium, potassium or ammonium,
if appropriate in the presence of a diluent and if appropriate in the presence of an acid, and
b) reacting the resulting triazolidinethione derivatives of the formula

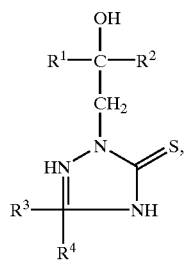

(V)

in which
R$^1$, R$^2$, R$^3$ and R$^4$ are each as defined above
with formic acid, if appropriate in the presence of a catalyst and is appropriate in the presence of a diluent.

It is extremely surprising that triazolinethione derivatives of the formula (I) can be prepared by the process according to the invention in substantially higher yields or under considerably more simple conditions than by the prior-art methods. It is also unexpected that, when the second step of the process according to the invention is carried out, the exchange of the

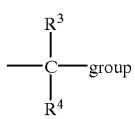

for a methylene group occurs with high selectivity.

The present according to the invention has a number of advantages. Thus, as already mentioned, it makes it possible to synthesize triazolinethiones of the formula (I) in high yield. It is also favorable that the required starting materials and reaction components can be prepared in a simple manner and are available even in relatively large amounts. Finally, a further advantage consists in the fact that the individual reaction steps can be carried out and the reaction products can be isolated without any problems.

Using 2(1-chloro-cyclopropyl)-3-(2-chloro-phenyl)-2-hydroxy-propyl-1-hydrazine as starting material and reacting this in the first step with acetone and potassium thiocyanate and, in the second step, allowing the resulting triazolidinethione derivative to react with formic acid, the course of the process according to the invention can be illustrated by the formula scheme below.

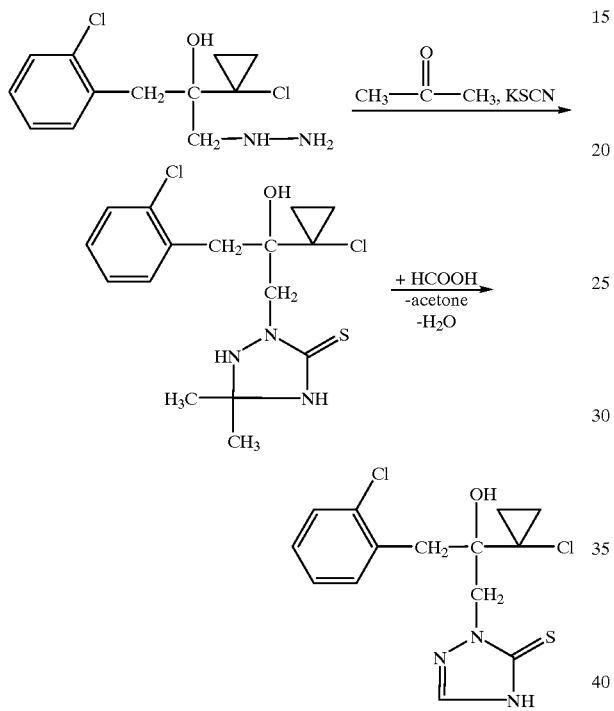

The formula (II) provides a general definition of the hydrazine derivatives required as starting materials for carrying out the process according to the invention. Preference is given to using compounds of the formula (II) in which $R^1$ represents straight-chain or branched alkyl having 1 to 6 carbon atoms, where these radicals may be mono- to tetrasubstituted by identical or different substituents from the group consisting of halogen, alkoxy having 1 to 4 carbon atoms, alkoximino having 1 to 4 carbon atoms in the alkoxy moiety and cycloalkyl having 3 to 7 carbon atoms, or represents straight-chain or branched alkenyl having 2 to 6 carbon atoms, where each o these radicals may be mono- to trisubstituted by identical or different substituents from the group consisting of halogen, alkoxy having 1 to 4 carbon atoms and cycloalkyl having 3 to 7 carbon atoms, or represents cycloalkyl having 3 to 7 carbon atoms, where each of these radicals may be mono- to trisubstituted by identical or different substituents from the group consisting of halogen, cyano and alkyl having 1 to 4 carbon atoms, or represents aralkyl having 6 to 10 carbon atoms in the aryl moiety and 1 to 4 carbon atoms in the straight-chain or branched alkyl moiety, where the aryl moiety may in each case the mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aralkenyl having 6 to 10 carbon atoms in the aryl moiety and 2 to 4 carbon atoms in the alkenyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkenyl moiety and 1 to 4 carbon atoms in the alkyl moiety, nitro and cyano, or represents aroxyalkyl having 6 to 10 carbon atoms in the aryl moiety and 1 to 4 carbon atoms in the straight-chain or branched oxyalkyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 to 2 carbon atoms and 1 to 5 identical or different halogen atoms, halogenoalkylthio having 1 to 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aryl having 6 to 10 carbon atoms, where each of these radicals may be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 to 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents an optionally benzo-fused five- or six-membered heteroaromatic radical having 1 to 3 heteroatoms, such as nitrogen, sulphur and/or oxygen, where each of these radicals may be mono- to trisubstituted by identical or different substituents from the group consisting of halogen, alkyl having 1 to 4 carbon atoms, hydroxyalkyl having 1 to 4 carbon atoms, hydroxyalkinyl having 3 to 8 carbon atoms, alkoxy having 1 to 3 carbon atoms, alkylthio having 1 or 2 carbon atoms, halogenoalkyl, halogenoalkoxy and halogenoalkylthio having in each case 1 or 2 carbon atoms and 1 to 5 identical or different halogen atoms, such as fluorine or chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkeny moiety, alkoximinoalkyl having 1 to 4 carbon atoms in the alkoxy moiety and 1 to 3 carbon atoms in the alkyl moiety, nitro and cyano, and $R^2$ represents straight-chain or branched alkyl having 1 to 6 carbon atoms, where these radicals may be mono- to tetrasubstituted by identical or different substituents from the group consisting of halogen, alkoxy having 1 to 4 carbon atoms, alkoximino having 1 to 4 carbon atoms in the alkoxy moiety and cycloalkyl having 3 to 7 carbon atoms, or represents straight-chain or branched alkyl having 2 to 6 carbon atoms, where each of these radicals may be mono- to trisubstituted by identical or different substituents from the group consisting of halogen, alkoxy having 1 to 4 carbon atoms and cycloalkyl having 3 to 7 carbon atoms, or represents cycloalkyl having 3 to 7 carbon atoms, where each of these radicals may be mono- to trisubstituted by identical or different substituents from the group consisting of halogen, cyano and alkyl having 1 to 4 carbon atoms, or represents aralkyl having 6 to 10 carbon atoms in the alkyl moiety and 1 to 4 carbon atoms in the straight-chain or branched alkyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aralkenyl having 6 to 10 carbon atoms in the aryl moiety and 2 to 4 carbon atoms in the alkenyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenalkylthio having 1 to 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aroxyalkyl having 6 to 10 carbon atoms in the aryl moiety and 1 to 4 carbon atoms in the straight chain or branched oxyalkyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 to 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aryl having 6 to 10 carbon atoms, where each of these radicals may be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents an optionally benzo-fused five- or six-membered heteroaromatic radical having 1 to 3 heteroatoms, such as nitrogen, sulphur and/or oxygen, where each of these radicals may be mono- to trisubstituted by identical or different substituents from the group consisting of halogen, alkyl having 1 to 4 carbon atoms, hydroxyalkyl having 1 to 4 carbon atoms, hydroxyalkinyl having 3 to 8 carbon atoms, alkoxy having 1 or 2 carbon atoms, alkylthio having 1 or 2 carbon atoms, halogenoalkyl, halogenoalkoxy and halogenoalkylthio having in each case 1 or 2 carbon atoms and 1 to 5 identical or different halogen atoms, such as fluorine or chlorine atoms, formyl, dialkoxymethyl having 1 to 2 carbon atoms in each alkoxy group, acyl having 2 to 4 carbon atoms, alkoxycarbonyl having 1 to 4 carbon atoms in the alkoxy moiety, alkoximino alkyl having 1 to 4 carbon atoms in the alkoxy moiety and 1 to 3 carbon atoms in the alkyl moiety, nitro and cyano.

Particular preference is given to using hydrazine derivatives of the formula (II) in which $R^1$ represents straight-chain or branched alkyl having 1 to 4 carbon atoms, where these radicals may be mono- to tetrasubstituted by identical or different substituents from the group consisting of fluorine, chlorine, bromine, methoxy, ethoxy, propoxy, isopropoxy, alkoximino having 1 to 2 carbon atoms in the alkoxy moiety, cyclopropyl, cyclobutyl, cyclopentyl and cyclohexyl, or represents straight-chain or branched alkenyl having 2 to 5 carbon atoms, where each of these radicals may be mono- to trisubstituted by identical or different substituents from the group consisting of fluorine, chlorine, bromine, methoxy, ethoxy, propoxy, isopropoxy, cyclopropyl, cyclopropyl, cyclobutyl, cyclopentyl and cyclohexyl, or represents cycloalkyl having 3 to 6 carbon atoms, where each of these radicals may be mono- to trisubstituted by identical or different substituents from the group consisting of fluorine, chlorine, bromine, cyano, methyl, ethyl, propyl, isopropyl and tert-butyl, or represents phenylalkyl having 1 to 4 carbon atoms in the straight-chain or branched alkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenylalkenyl having 2 to 4 carbon atoms in the alkenyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, chloroxycarbonyl, methoxyiminomethyl, 1-methoxyiminoethyl, nitro and cyano, or represents phenoxyalkyl having 1 to 4 carbon atoms in the straight-chain or branched oxyalkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chorodifluoromethylthio, methoxycarbonyl, ethoxycarbonyl, methoximinomethyl, 1-methoxyiminoethyl, nitro and cyano, or represents phenyl which may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoxyiminomethyl, 1-methoximinoethyl, nitro and cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, where each of these radicals may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro, cyano, formyl, dimethoxymethyl, acetyl and propionyl, and $R^2$ represents straight-chain or branched alkyl having 1 to 4 carbon atoms, where these radicals may be mono- to tetrasubstituted by identical or different substituents from the group consisting of fluorine, chlorine, bromine, methoxy, ethoxy, propoxy, isopropoxy, alkoximino having 1 or 2 carbon atoms in the alkoxy moiety, cyclopropyl, cyclobutyl, cyclopentyl and cyclohexyl, or represents straight-chain or branched alkenyl having 2 to 5 carbon atoms, where each of these radicals may be mono- to trisubstituted by identical or different substituents from the group consisting of fluorine, chlorine, bromine, methoxy, ethoxy, propoxy, isopropoxy, cyclopropyl, cyclobutyl, cyclopentyl and cyclohexyl, or represents cycloalkyl having 3 to 6 carbon atoms, where each of these radicals may be mono- to trisubstituted by identical or different substituents from the group consisting of fluorine, chlorine, bromine, cyano, methyl, ethyl, propyl, isopropyl and tert-butyl, or represents phenylalkyl having 1 to 4 carbon atoms in the straight-chain or branched alkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenylalkenyl having 2 to 4 carbon atoms in the alkenyl moiety, where the phenyl moiety may be mono- to trisubstituted by identical or different substituents from the group consisting of fluorine, chlorine, bromine, methyl, ethyl, tert-butyl, ethoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenoxyalkyl having 1 to 4 carbon atoms in the straight-chain or branched oxyalkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoxyiminoethyl, nitro and cyano, or represents phenyl which may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, where each of these radicals may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro, cyano, formyl, dimethoxymethyl, acetyl and propionyl.

Very particular preference is given to using hydrazine derivatives of the formula (II) in which $R^1$ represents n-propyl, isopropyl, n-butyl, i-butyl, sec-butyl or tert-butyl, where these radicals may be mono- to tetrasubstituted by identical or different substituents from the group consisting of fluorine, chlorine, bromine, methoxy, ethoxy, propoxy, isopropoxy, methoximino, ethoximino, cyclopropyl, cyclobutyl, cyclopentyl and cyclohexyl, or represents straight-chain or branched alkenyl having 2 to 5 carbon atoms, where each of these radicals may be mono-to trisubstituted by identical or different substituents from the group consisting of fluorine, chlorine, bromine, methoxy, ethoxy, property, isopropoxy, cyclopropyl, cyclobutyl, cyclopentyl and cyclohexyl, or represents 1-methoxy-cyclohexyl, cyclohexyl, 1-chloro-cyclopropyl, 1-fluoro-cyclopropyl, 1-methyl-cyclopropyl, 1-cyano-cyclopropyl, cyclopropyl, 1-methyl-cyclopentyl or 1-ethyl-cyclopentyl, or represents phenylalkyl having 1 or 2 carbon atoms in the straight-chain or branched alkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenylalkenyl having 2 to 4 carbon atoms in the alkenyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluormethoxy, difluoromethoxy, chlorodifluoromethylthio, methoxycarbonyl, ethoxycarbonyl, methoximinomethyl, 1-methoximinoethyl, nitro and cyano, or represents phenoxyalkyl having 1 to 4 carbon atoms in the straight-chain or branched oxyalkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenyl which may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, where each of these radicals may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro, cyano, formyl, dimethoxymethyl, acetyl and propionyl, and $R^2$ represents n-propyl, isopropyl, n-butyl, i-butyl, sec-butyl, or tert-butyl, where these radicals may be mono- to tetrasubstituted by identical or different substituents from the group consisting of fluorine, chlorine, bromine, methoxy, ethoxy, propoxy, isopropoxy, methoximino, ethoximino, cyclopropyl, cyclobutyl, cyclopentyl and cyclohexyl, or represents straight-chain or branched alkenyl having 2 to 5 carbon atoms, where each of these radicals may be mono- to trisubstituted by identical or different substituents from the group consisting of fluorine, chlorine, bromine, methoxy, ethoxy, propoxy, isopropoxy, cyclopropyl, cyclobutyl, cyclopentyl and cyclohexyl, or represents 1-methyl-cyclohexyl, cyclohexyl, i-chloro-cyclopropyl, 1-fluoro-cyclopropyl, 1-methyl-cyclopropyl, 1-cyano-cyclopropyl, cyclopropyl, 1-methyl-cyclopentyl, or 1-ethyl-cyclopentyl, or represents phenylalkyl having 1 to 2 carbon atoms in the straight-chain or branched alkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenylalkenyl having 2 to 4 carbon atoms in the alkenyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoxyiminomethyl, 1-methoximinoethyl, nitro and cyano, or represents phenoxyalkyl having 1 to 4 carbon atoms in the straight-chain or branched oxyalkyl moiety, where the phenyl moiety may be mono- to trisubstituted by identical or different substituents from the group consisting of fluorine, chlorine, bromine methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenyl which may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, where each of these radicals may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro, cyano, formyl, dimethoxymethyl, acetyl and/propionyl.

The hydrazine derivatives of the formula (II) are known or can be prepared by processes known in principle (cd. DE-A-40 30 039).

Thus, hydrazine derivatives of the formula (II) are obtained by reacting 1-chloro-2-hydroxy-ethane derivatives of the formula

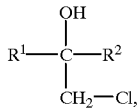

(VI)

or oxirane derivatives of the formula

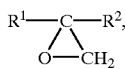

(VII)

in which

R¹ and R² are each as defined above with hydrazine hydrate, if appropriate in the presence of a diluent.

The 1-chloro-2-hydroxy-ethane derivatives of the formula (VI) and also the oxirane derivatives of the formula (VII) are known or can be prepared by processes known in principle (cf. DE-A-40 30 039 and EP-A 0 297 345).

Suitable diluents for the above process for preparing hydrazine derivatives of the formula (II) are all customary inert organic solvents. Preference is given to using alcohols, such as methanol, ethanol or n-butanol, furthermore ethers, such as dioxane or methyl tert-butyl ether, and also aromatic hydrocarbons, such as benzene, toluene or xylene. However, it is also possible to carry out the reaction without any additional solvent. In this case, an excess of hydrazine hydrate is employed, so that it acts both as reaction component and as diluent.

When carrying out the preparation of hydrazine derivatives of the formula (II) according to the above process, the reaction temperatures can be varied within a certain range. In general, the process is carried out at temperatures between 60° C. and 120° C., preferably between 70° C. and 110° C.

In the preparation of hydrazine derivatives of the formula (II) according to the above process, in general from 1 to 20 mol, preferably from 5 to 15 mol, of hydrazine hydrate are employed per mole of 1-chloro-2-hydroxy-ethane derivative of the formula (VI) or of oxirane derivative of the formula (VII). Work-up is carried out by customary methods. In general, the reaction mixture is admixed with an organic solvent which is sparingly water-miscible, such as methyl tert-butyl ether or toluene, the aqueous phase is removed and the organic phase is washed and dried.

The formula (III) provides a general definition of the carbonyl compounds required as reaction components for carrying out the first step of the process according to the invention. Preference is given to using carbonyl compounds of the formula (III) in which $R^3$ represents methyl, ethyl, n-propyl, isopropyl, n-butyl, tert-butyl or phenyl and $R^4$ represents hydrogen, methyl, ethyl, n-propyl or n-butyl or $R^3$ and $R^4$ together represent a —$(CH_2)_5$— chain.

Particular preference is given to carbonyl compounds of the formula (III) in which $R^3$ represents methyl, ethyl, n-propyl, isopropyl, tert-butyl or phenyl and $R^4$ represents hydrogen, methyl, ethyl or n-propyl or $R^3$ and $R^4$ together represents a —$(CH_2)_5$— chain.

Examples of carbonyl compounds of the formula (III) which may be mentioned are:
acetaldehyde
propionaldehyde
benzaldehyde
acetone
diethyl ketone
methyl ethyl ketone
di-n-propyl ketone
pinacolone
acetophenone and
cyclohexanone.

The carbonyl compounds of the formula (III) and also thiocyanates of the formula (IV) are known.

Suitable diluents for carrying out the first step of the process according to the invention are all inert organic solvents which are customary for such reactions. Preference is given to using aromatic hydrocarbons, such as benzene, toluene or xylene, furthermore ethers, such as dioxane, methyl tert-butyl ether, 1,2-dimethoxy-ethane or methyl tert-amyl ether, moreover esters, such as ethyl acetate or butyl acetate, and also alcohols, such as a propanol, butanol or pentanol. However, excess carbonyl compound of the formula (III) may also act as diluent.

Suitable acids for carrying out the first step of the process according to the invention are customary inorganic or organic acids. Preference is given to using hydrochloric acid, sulphuric acid or p-toluenesulphonic acid.

When carrying out the first step of the process according to the invention, the reaction temperatures can be varied within a relatively wide range. In general, the reaction is carried out at temperatures between 0° C. and 120° C., preferably between 10° C. and 110° C.

Both the first and the second step of the process according to the invention are generally carried out under atmosphere pressure. However, it is also possible to operate under elevated pressure or, if no gaseous components are involved in the reaction, under reduced pressure.

When carrying out the first step of the process according to the invention, generally 1 to 2 mol of carbonyl compound of the formula (III) and 1 to 2 mol of thiocyanate of the formula (IV) are employed per mole of hydrazine derivative of the formula (II). Work-up is carried out by customary methods. In general, the reaction mixture is washed with water, the organic phase is dried and concentrated and the residue that remains is freed from undesirable components by customary methods, for example by recrystallization.

The formula (V) provides a general definition of the triazolidinethione derivatives required as starting materials for carrying out the second step of the process according to the invention. In this formation, $R^1$, $R^2$, $R^3$ and $R^4$ each preferably have those meanings which have already been mentioned in connection with the description of the hydrazine derivatives of the formula (II) or the carbonyl compounds of the formula (III) as being preferred for these radicals.

The triazolidinethione derivatives of the formula (V) have hitherto not been disclosed. They can be prepared by the reaction of the first step of the process according to the invention.

Suitable catalysts for carrying out the second step of the process according to the invention are all reaction promoters which are customary for such reactions. Preference is given to using acids, such as hydrochloric acid, sulphuric acid or p-toluenesulphonic acid, and also metal oxides, such as amorphous titanium dioxide.

Suitable diluents for carrying out the second step of the process according to the invention are all weakly polar organic solvents which are customary for such reactions. Preference is given to using alcohols, such as propanol, butanol or pentanol, furthermore esters, such as ethyl acetate, butyl acetate or isobutyl formate, moreover ethers, such as 1,2-dimethoxyethane, methyl tert-butyl ether or methyl tert-amyl ether, and also an excess of formic acid.

When carrying out the second step of the process according to the invention, the reaction temperature can be varied within a certain range. In general, the reaction is carried out at temperatures between 80° C. and 150° C., preferably between 90° C. and 130° C.

When carrying out the second step of the process according to the invention, an excess, in general from 5 to 50 mol, of formic acid and, if appropriate, a small amount of catalyst is employed per mole of triazolidimethione derivative of the formula (V). Work-up is carried out by customary methods. In general, the reaction mixture is, if appropriate after prior dilution with an organic solvent which is sparingly water-miscible, extracted with aqueous hydrochloric acid, and the organic phase is dried and concentrated. Any impurities which may then still be present can be removed by customary methods, such as recrystallization.

In a particular variant, the process according to the invention can be carried out such that 1-chloro-2-hydroxy-ethane derivatives of the formula (VI) or oxirane derivatives of the formula (VII) are reacted with hydrazine hydrate and the resulting hydrazine derivatives of the formula (II) are then reacted further without prior isolation and purification. Accordingly, triazolimethione derivatives of the formula (I) can also be prepared by reacting 1-chloro-2-hydroxy-ethane derivatives of the formula

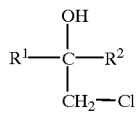

(VI)

or oxirane derivatives of the formula

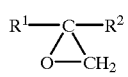

(VII)

in which $R^1$ and $R^2$ are each as defined above with hydrazine hydrate, if appropriate in the presence of a diluent, and reacting the resulting hydrazine derivatives of the formula

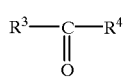

(II)

in which $R^1$ and $R^2$ are each as defined above without prior isolation with carbonyl compounds of the formula

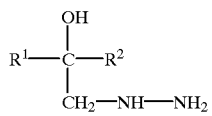

(III)

in which $R^3$ represents alkyl having 1 to 4 carbon atoms or represents phenyl and $R^4$ represents hydrogen or alkyl having 1 to 4 carbon atoms or $R^3$ and $R^4$ together represent a —(CH$_2$)$_5$— chain, and with thiocyanate of the formula

 X—SCN (IV)

in which

X represents sodium, potassium or ammonium, if appropriate in the presence of a diluent and if appropriate in the presence of an acid, and reacting the resulting triazolidinethione derivatives of the formula

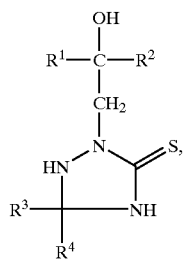

in which

R$^1$, R$^2$, R$^3$ and R$^4$ are each as defined above with formic acid, if appropriate in the presence of a catalyst and if appropriate in the presence of a diluent.

The individual steps of this process are carried out in the manner already described above.

The triazolinethione derivatives preparable according to the invention can be present in the "thiono" form of the formula

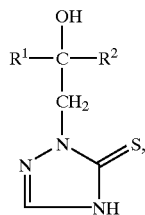

or in the tautomeric "mercapto" form of the formula

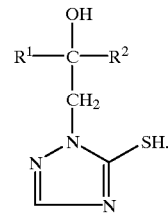

For the sake of simplicity, only the "thiono" form is shown in each case.

the triazolinethione derivatives preparable according to the invention are known as active compounds having microbicidal, in particular fungicidal, properties (cf. WO-A 96-15 048).

The practice of the process according to the invention is illustrated by the examples below.

PREPARATION EXAMPLES

Example 1

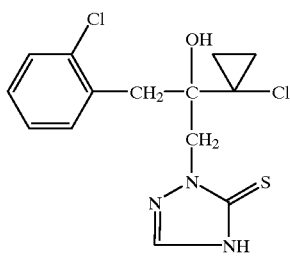

a) Preparation of the compound of the formula

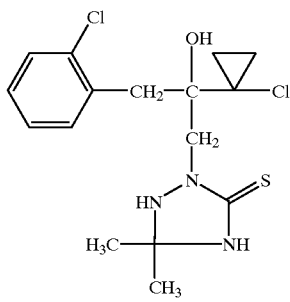

At room temperature and with stirring, a mixture of 27.5 g (0.1 mol) of 2-(1-chloro-cyclopropyl)-3-(2-chloro-phenyl)-2-hydroxy-propyl-1-hydrazine and 300 ml of 2N aqueous hydrochloric acid is initially admixed with 8.2 g (0.14 mol) of acetone and then with 13.6 g (0.14 mol) of potassium thiocyanate. The reaction mixture is then admixed with 100 ml of toluene and stirred at room temperature for another 10 hours. The resulting solid is then filtered off, washed with water and then with toluene and dried. In this manner, 30.7 g (82.1 % of theory) of the triazolidinethione derivative are obtained in the form of a colourless crystalline solid of melting point 186 to 189° C.

b) Preparation of the compound of the formula

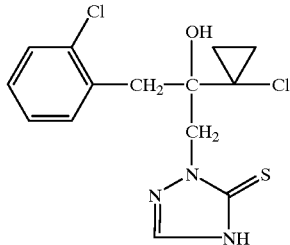

At room temperature and with stirring, a mixture of 92 g of formic acid and 100 ml of isobutyl formate is admixed with 18.7 g (0.05 mol) of the triazolidinethione derivative described under a). After the addition has ended, the reaction mixture is heated under reflux for 17 hours, then concentrated by distilling off excess formic acid and solvent and finally freed of volatile components under high vacuum. The product that remains is dissolved in toluene, the resulting solution is washed with water, and the organic phase is dried over sodium sulphate and concentrated by distilling off the solvent. In this manner, 14.2 g (76% of theory) of 2-(1-chloro-cyclopropyl)-1-(2-chloro-phenyl)-3-(4,5-dihydro-1, 2,4-triazole-5-thiono-1-yl)-propyl-2-ol are obtained in the form of a solid of melting point 138 to 139° C.

Example 2

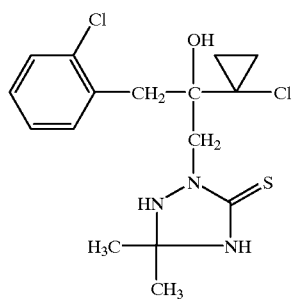

At room temperature and with stirring, 22 g (=0.05 mmol) of a product comprising 63.7% of 1-chloro-2-hydroxy-ethane are added dropwise over a period of 15 minutes to 25 g (0.5 mol) of hydrazine hydrate. After the addition has ended, the reaction mixture is stirred at 100° C. for 2 hours and then cooled to room temperature. The resulting mixture is stirred into 100 ml of water and the aqueous phase is decanted off from the solid precipitate. This process is repeated once more using 100 ml of water. The resulting product is admixed with 150 ml of 2N aqueous hydrochloric acid, 4.1 g (0.07 mol) of acetone, 6.8 g (0.07 mol) of potassium thiocyanate and 50 ml of toluene. The reaction mixture is stirred at room temperature for 12 hours and then filtered. The filter residue is washed successively with water and toluene and then dried. In this manner, 11.6 g of triazolidinethione derivative of the abovementioned formula are obtained in the form of a colourless crystalline solid of melting point 186 to 187° C. The calculated yield is 62.0% of theory, based on the 1-chloro-2-hydroxy-ethane employed.

The triazolidinethione derivatives listed in the table below are likewise prepared by the method given in Example 2.

TABLE 1

(Va)

| Ex. No. | R³ | R⁴ | Melting point [°C.] | Yield in % of theory |
|---|---|---|---|---|
| 3 | —CH₃ | H | 143–146 | 52.6 |
| 4 | —CH₃ | —C₂H₅ | 167 (decomp.) | 72.5 |
| 5 | phenyl | —CH₃ | 174 (decomp.) | 66.4 |
| 6 | —(CH₂)₅— | | 194–196 | 67.9 |

TABLE 1-continued (Va)

| Ex. No. | R³ | R⁴ | Melting point [°C.] | Yield in % of theory |
|---|---|---|---|---|
| 7 | —C(CH₃)₃ | —CH₃ | (decomp.) 137 (decomp.) | 59.3 |
| 8 | —CH(CH₃)₂ | —CH₃ | 146–152 | 68.2 |
| 9 | phenyl | H | 176 | 38 |

COMPARATIVE EXAMPLES

Example A

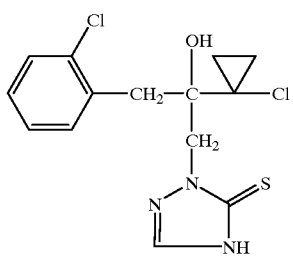

At −20° C., a mixture of 3.12 g (10 mmol) of 2-(1-chloro-cyclopropyl)-1-(2-chlorophenyl)-3-(1,2,4-triazol-1-yl)-propan-2-ol and 45 ml of absolute tetrahydrofuran is admixed with 8.4 ml (21 mmol) of n-butyl-lithium in hexane and stirred at 0° C. for 30 minutes. The reaction mixture is then cooled to −70° C., admixed with 0.32 g of (10 mmol) of sulphur powder and stirred at −70° C. for 30 minutes. The mixture is warmed to −10° C., admixed with ice-water and adjusted to pH 5 by addition of dilute sulphuric acid. The mixture is extracted repeatedly with ethyl acetate, and the combined organic phases are dried over sodium sulphate and concentrated under reduced pressure. In this manner, 3.2 g of a product which, according to gaschromatographic analysis, comprises 95% of 2-(1-chloro-cyclopropyl)-1-(2-chloro-phenyl)-3-(4,5-dihydro-1,2,4-triazol-5-thiono-1-yl)-propan-2-ol are obtained. Recrystallization from toluene gives this substance as a solid which melts at from 138 to 139° C.

Example B

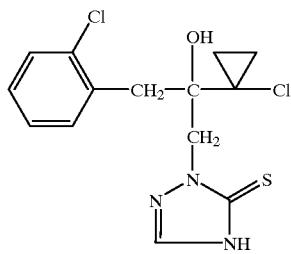

with stirring, a mixture of 3.12 g (10 mmol) of 2-(1-chloro-cyclopropyl)-1-(2-chloro-phenyl)-3-(1,2,4-triazol-1-yl)-propan-2-ol, 0.95 g (30 mmol) of sulphur powder and 20 ml of absolute N-methyl-pyrrolidone is heated at 200° C. for 44 hours. The reaction mixture is then concentrated under reduced pressure (0.2 mbar). The resulting crude product (3.1 g) is recyrstallized from toluene. In this manner, 0.7 g (20% of theory) of 2-(1-chloro-cyclopropyl)-1-(2-chlorophenyl)-3-(4,5-dihydro-1,2,4-triazol-5-thiono-1-yl)-propan-2-ol is obtained in the form of a solid which melts at 138–139° C.

What is claimed is:

1. A triazolidinethione derivative of the formula

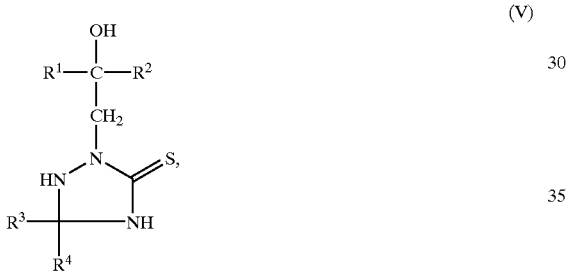

in which $R^1$ represents straight-chain or branched alkyl having 1 to 6 carbon atoms, where these radicals may be mono- to tetrasubstituted by identical or different substituents from the group consisting of halogen, alkoxy having 1 to 4 carbon atoms, alkoximino having 1 to 4 carbon atoms in the alkoxy moiety and cycloalkyl having 3 to 7 carbon atoms, or represents straight-chain or branched alkenyl having 2 to 6 carbon atoms, where each of these radicals may be mono- to trisubstituted by identical or different substituents from the group consisting of halogen, alkoxy having 1 to 4 carbon atoms and cycloalkyl having 3 to 7 carbon atoms, or represents cycloalkyl having 3 to 7 carbon atoms, where each of these radicals may be mono- to trisubstituted by identical or different substituents from the group consisting of halogen, cyano and alkyl having 1 to 4 carbon atoms, or represents aralkyl having 6 to 10 carbon atoms in the aryl moiety and 1 to 4 carbon atoms in the straight-chain or branched alkyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aralkenyl having 6 to 10 carbon atoms in the aryl moiety and 2 to 4 carbon atoms in the alkenyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, represents aroxyalkyl having 6 to 10 carbon atoms in the aryl moiety and 1 to 4 carbon atoms in the straight-chain or branched oxyalkyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aryl having 6 to 10 carbon atoms, where each of these radicals may be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, and R² represents straight-chain or branched alkyl having 1 to 6 carbon atoms, where these radicals may be mono- to tetrasubstituted by identical or different substituents from the group consisting of halogen, alkoxy having 1 to 4 carbon atoms, alkoximino having 1 to 4 carbon atoms in the alkoxy moiety and cycloalkyl having 3 to 7 carbon atoms, or represents straight-chain or branched alkenyl having 2 to 6 carbon atoms, where each of these radicals may be mono- to trisubstituted by identical or different substituents from the group consisting of halogen, alkoxy having 1 to 4 carbon atoms and cycloalkyl having 3 to 7 carbon atoms, or represents cycloalkyl having 3 to 7 carbon atoms, where each of these radicals may be mono- to trisubstituted by identical or different substituents from the group consisting of halogen, cyano and alkyl having 1 to 4 carbon atoms, or represents aralkyl having 6 to 10 carbon atoms in the alkyl moiety and 1 to 4 carbon atoms in the straight-chain or branched alkyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aralkenyl having 6 to 10 carbon atoms in the aryl moiety and 2 and 4 carbon atoms in the alkenyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aroxyalkyl having 6 to 10 carbon atoms in the aryl moiety and 1 to 4 carbon atoms in the straight-chain or branched oxyalkyl moiety, where the aryl moiety may in each case be mono- to trisubstituted by identical or different substituents from the group consisting of halogen, alkyl having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aryl having 6 to 10 carbon atoms, where each of these radicals may be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in thealkoxy moiety, alkoximinoalkyl having 1 to 4 carbon atoms in the alkoxy moiety and 1 to 4 carbon atoms in the alkyl moiety, nitro and cyano and R³ represents alkyl having 1 to 4 carbon atoms or phenyl and R⁴ represents hydrogen or alkyl having 1 to 4 carbon atoms or R³ and R⁴ together represent a —(CH₂)₅— chain.

2. A triazolidinethione derivative of the formula

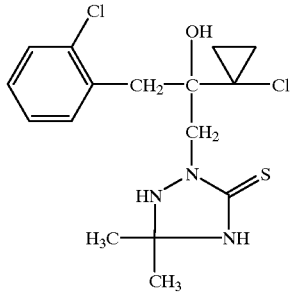

3. The triazolidinethione of claim 1 wherein

R³ represents methyl, ethyl, n-propyl, isopropyl, n-butyl, ter-butyl or phenyl and R⁴ represents hydrogen, methyl, ethyl, n-propyl or n-butyl or R³ and R⁴ together represent a —(CH₂)₅— chain.

4. The triazolidinethione of claim 1 wherein

R³ represents methyl, ethyl, n-propyl, isopropyl, tert-butyl or phenyl and

R⁴ represents hydrogen, methyl, ethyl or n-propyl or R³ and R⁴ together represent a —(CH₂)₅— chain.

5. The triazolidinethione of claims 1, 3 or 4 wherein

R¹ represents straight-chain or branched alkyl having 1 to 4 carbon atoms, where these radicals may be mono- to tetrasubstituted by identical or different substituents from the group consisting of fluorine, chlorine, bromine, methoxy, ethoxy, propoxy, isopropoxy, alkoximino having 1 or 2 carbon atoms in the alkoxy moiety, cyclopropyl, cyclobutyl, cyclopentyl and cyclohexyl, or
represents straight-chain or branched alkenyl having 2 to 5 carbon atoms, where each of these radicals may be mono- to trisubstituted by identical or different substituents from the group consisting of fluorine, chlorine, bromine, methoxy, ethoxy, propoxy, isopropoxy, cyclopropyl, cyclobutyl, cyclopentyl and cyclohexyl, represents cycloalkyl having 3 to 6 carbon atoms, where each of these radicals may be mono- to trisubstituted by identical or different substituents from the group consisting of fluorine, chlorine, bromine, cyano, methyl, ethyl, propyl, isopropyl and tert-butyl, or
represents phenylalkyl having 1 to 4 carbon atoms in the straight-chain or branched alkyl moiety, where the phenyl moiety may be mono- to trisubstituted by identical or different substituents from the group consisting of fluorine, chlorine, bromine, methyl, ethyl tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or
represents phenylalkenyl having 2 to 4 carbon atoms in the alkenyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or
represents phenoxyalkyl having 1 to 4 carbon atoms in the straight-chain or branched oxyalkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or
represents phenyl which may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, and
$R^2$ represents straight-chain or branched alkyl having 1 to 4 carbon atoms, where these radicals may be mono- to tetrasubstituted by identical or different substituents from the group consisting of fluorine, chlorine, bromine, methoxy, ethoxy, propoxy, isopropoxy, alkoximino having 1 or 2 carbon atoms in the alkoxy moiety, cyclopropyl, cyclobutyl, cyclopentyl and cyclohexyl, or
represents straight-chain or branched alkenyl having 2 to 5 carbon atoms, where each of these radicals may be mono- to trisubstituted by identical or different substituents from the group consisting of fluorine, chlorine, bromine, methoxy, ethoxy, propoxy, isopropoxy, cyclopropyl, cyclobutyl, cyclopentyl and cyclohexyl, or
represents cycloalkyl having 3 to 6 carbon atoms, where each of these radicals may be mono- to trisubstituted by identical or different substitutents from the group consisting of fluorine, chlorine, bromine, cyano, methyl, ethyl, propyl, isopropyl and tert-butyl, or
represents phenylalkyl having 1 to 4 carbon atoms in the straight-chain or branched alkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or
represents phenylalkenyl having 2 to 4 carbon atoms in the alkenyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or
represents phenoxyalkyl having 1 to 4 carbon atoms in the straight-chain or branched oxyalkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or
represents phenyl which may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano.

6. The triazolidinethione of claims 1, 3 or 4 wherein $R^1$ represents n-propyl, isopropyl, n-butyl, i-butyl, sec-butyl or tert-butyl, where these radicals may be mono- to tetrasubstituted by identical or different substituents from the group consisting of fluorine, chlorine, bromine, methoxy, ethoxy, propoxy, isopropoxy, methoximino, ethoximino, cyclopropyl, cyclobutyl, cyclopentyl and cyclohexyl, or represents straight-chain or branched alkenyl having 2 to 5 carbon atoms, where each of these radicals may be mono- to trisubstituted by identical or different substituents from the group consisting of fluorine, chlorine, bromine, methoxy, ethoxy, propoxy, isopropoxy, cyclopropyl, cyclobutyl, cyclopentyl and cyclohexyl, or represents 1-methyl-cyclohexyl, cyclohexyl 1-chloro-cyclopropyl, 1-fluoro-cyclopropyl, 1-methyl-cyclopropyl, 1-cyano-cyclopropyl, cyclopropyl, 1-methyl-cyclopentyl or 1-ethyl-cyclopentyl, or represents phenylalkyl having 1 or 2 carbon atoms in the straight-chain or branched alkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenylalkenyl having 2 to 4 carbon atoms in the alkenyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenoxyalkyl having 1 to 4 carbon atoms in the straight-chain or branched oxyalkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenyl which may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, and $R^2$ represents n-propyl, isopropyl, n-butyl, i-butyl, sec-butyl or tert-butyl, where these radicals may be mono- to tetrasubstituted by identical or different substituents from the group consisting of fluorine, chlorine, bromine, methoxy, ethoxy, propoxy, isopropoxy, methoximino, ethoximino, cyclopropyl, cyclobutyl, cyclopentyl and cyclohexyl, or represents straight-chain or branched alkenyl having 2 to 5 carbon atoms, where each of these radicals may be mono- to trisubstituted by identical or different substituents from the group consisting of fluorine, chlorine, bromine, methoxy, ethoxy, propoxy, isopropoxy, chloropropyl, cyclobutyl, cyclopentyl and cyclohexyl, or represents 1-methyl-cyclohexyl, cyclohexyl, 1-chloro-cyclopropyl, 1-fluoro-cyclopropyl, 1-methyl-cyclopropyl, 1-cyano-cyclopropyl, cyclopropyl, 1-methyl-cyclopentyl or 1-ethyl-cyclopentyl, or represents phenylalkyl having 1 or 2 carbon atoms in the straight-chain or branched alkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenylalkenyl having 2 to 4 carbon atoms in the alkenyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenoxyalkyl having 1 to 4 carbon atoms in the straight-chain or branched oxyalkyl moiety, where the phenyl moiety may be mono- to trisubstituted by identical or different substituents from the group consisting of fluorine, chlorine, bromine methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenyl which may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano.

* * * * *